(12) United States Patent
Remias et al.

(10) Patent No.: US 7,786,318 B2
(45) Date of Patent: Aug. 31, 2010

(54) CATALYST PREPARATION

(75) Inventors: Joseph E. Remias, Havertown, PA (US);
Edrick Morales, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 761 days.

(21) Appl. No.: 11/104,122

(22) Filed: Apr. 12, 2005

(65) Prior Publication Data

US 2006/0229460 A1    Oct. 12, 2006

(51) Int. Cl.
*C07D 301/06* (2006.01)
(52) U.S. Cl. ........................ 549/533; 549/522
(58) Field of Classification Search ............... 549/533, 549/532, 573; 502/66, 107, 242
See application file for complete search history.

(56) References Cited

U.S. PATENT DOCUMENTS

| | | | |
|---|---|---|---|
| 4,410,501 A | 10/1983 | Taramasso et al. | |
| 6,008,389 A | 12/1999 | Grosch et al. | |
| 6,475,465 B2 * | 11/2002 | Lin et al. | 423/716 |
| 6,498,259 B1 | 12/2002 | Grey et al. | |
| 6,555,493 B2 | 4/2003 | Cooker et al. | |
| 6,759,540 B2 * | 7/2004 | Oguchi et al. | 549/529 |
| 6,841,144 B2 | 1/2005 | Hasenzahl et al. | |
| 2003/0035771 A1 | 2/2003 | Hasenzahl | 423/713 |
| 2004/0059139 A1 * | 3/2004 | Cooker et al. | 549/531 |

* cited by examiner

*Primary Examiner*—Janet L Andres
*Assistant Examiner*—Raymond Covington
(74) *Attorney, Agent, or Firm*—Yuanzhang Han

(57) ABSTRACT

Titanium silicallite crystals useful as catalyst for the production of propylene oxide are prepared by forming a solution of a silicon component, a titanium component and a template, the mol ratio of template to silicon component being 0.25 or less and heating the solution to reaction temperature at a rate not to exceed 0.3° C./min.

8 Claims, 1 Drawing Sheet

CATALYST PREPARATION

FIELD OF THE INVENTION

The present invention relates to the preparation of titanium silicalite (TS-1) which has improved utility, for example, as a catalyst for the oxidation of propylene to form propylene oxide.

DESCRIPTION OF THE PRIOR ART

The preparation of TS-1 is, by now, a well known procedure. Patents illustrating TS-1 preparation include U.S. Pat. Nos. 4,410,501, and 6,008,389, as well as the references cited in U.S. Pat. No. 6,498,259. See also U.S. Pat. No. 6,841,144.

Preparation procedures commonly employed involve preparing a reaction mixture comprised of water, a silica source, a titanium source and a quaternary ammonium compound. The reaction mixture is heated to reaction temperature and maintained at the reaction temperature for a time sufficient to form the desired crystals of TS-1. The crystals are normally washed, dried and calcined prior to use, for example, as catalyst in the production of propylene oxide.

There are a number of important considerations involved in the production of TS-1 for use as a catalyst in a propylene oxide process. The product must show high activity as catalyst for the production of propylene oxide but at the same time, for economic reasons, the catalyst must be easily prepared and as inexpensive as possible insofar as the materials used in its production are concerned.

In the prior art practices, widely varying relative amounts of the reaction mixture components have been employed. U.S. Pat. No. 4,410,501 in the table at column 1 describes various ratios of the critical reaction components. Ratios of $SiO_2/TiO_2$ ranging from 5-200 are described whereas ratios of the quaternary ammonium template compound to $SiO_2$ of 0.1-2.0 (i.e. 1/10 -2/1) are taught. U.S. Pat. No. 6,841,144 emphasizes use of template to $SiO_2$ ratios of 0.12 to less than 0.20. Also when the reaction mixture is prepared, usually it is rapidly heated (ramped) to the reaction temperature of 160-190° C. and maintained at this temperature for an extended period which may be measured in days or even weeks. U.S. Pat. No. 6,008,389, for example, in Example 1 describes the preparation of TS-1 using a quatenary ammonium compound to $SiO_2$ mol ratio of 0.360, ramping the temperature of the reaction mixture to 175° C. at a heating rate of 3° C./min and maintaining the reactor mixture at 175° C. for 92 hours to form the TS-1 product.

The cost of the reagents used in the TS-1 preparation is, of course, an important consideration. Since the cost of TS-1 preparation is very heavily dependent on the relative amount of the quaternary ammonium reaction component, it is advantageous to minimize this component to the extent possible. However, to some extent the activity of the product TS-1 as a catalyst for propylene oxide production is affected by the relative amounts of reagents employed. In addition, the rate at which the reaction mixture from which the TS-1 crystals are formed is ramped (heated) to reaction temperature has been found to exert a vital role in the catalyst characteristics of the product TS-1.

In accordance with the present invention, TS-1, which is highly active as catalyst for propylene oxide production, is formed while minimizing the cost of the reagents and a preparation procedure is provided which can readily be scaled up to commercial operation.

BRIEF DESCRIPTION OF THE INVENTION

In accordance with the invention TS-1 is formed by reacting a silicon component, illustratively tetraethyl orthosilicate, and a titanium component, illustratively tetraethyl orthotitanate, in the presence of a quaternary ammonium compound template such as tetrapropylammonium hydroxide. A key feature is control of the tetrapropylammonium hydroxide (TPA) to silicon component molar ratio to a value not to exceed about 0.25, preferably not to exceed about 0.19, while at the same time providing a low temperature ramping rate of the reaction mixture, not to exceed about 0.3° C./min, preferably not to exceed about 0.2° C./min. It has been found that by following these guidelines, a TS-1 product is produced which has high catalytic activity for the production of propylene oxide. At the same time, due to the low $TPA/SiO_2$ ratio, costs associated with the expensive TPA component are maintained at an attractively low level. A further advantage is that the instant procedure can more readily be scaled up to the commercial level since the slower heating or ramping rates are generally easier to achieve on a large scale.

The TS-1 crystals prepared in accordance with the present invention can vary substantially in average particle size although the average particle size does not correlate with catalytic activity. For example, TS-1 prepared in accordance with the invention with a molar ratio of TPA to silicon compound of 0.14 at a temperature ramping rate of 0.17° C./min had an average particle size quite similar (0.2-0.3 microns diameter) to that of a TS-1 prepared using a TPA to silicon compound ratio of 0.45 at a temperature ramping rate of 0.49° C./min. When used as a catalyst for the oxidation of propylene to propylene oxide, however, the TS-1 prepared according to the invention with the molar ratio of TPA to silicon compound of 0.14 was a surprisingly superior catalyst as compared to the 0.45 ratio material.

In general, it appears that for the template to $SiO_2$ ratios lower than 0.25 smaller particle size crystals are formed as the temperature ramp rate is decreased whereas this trend is not observed at the higher ratios.

DETAILED DESCRIPTION

Figure 1:
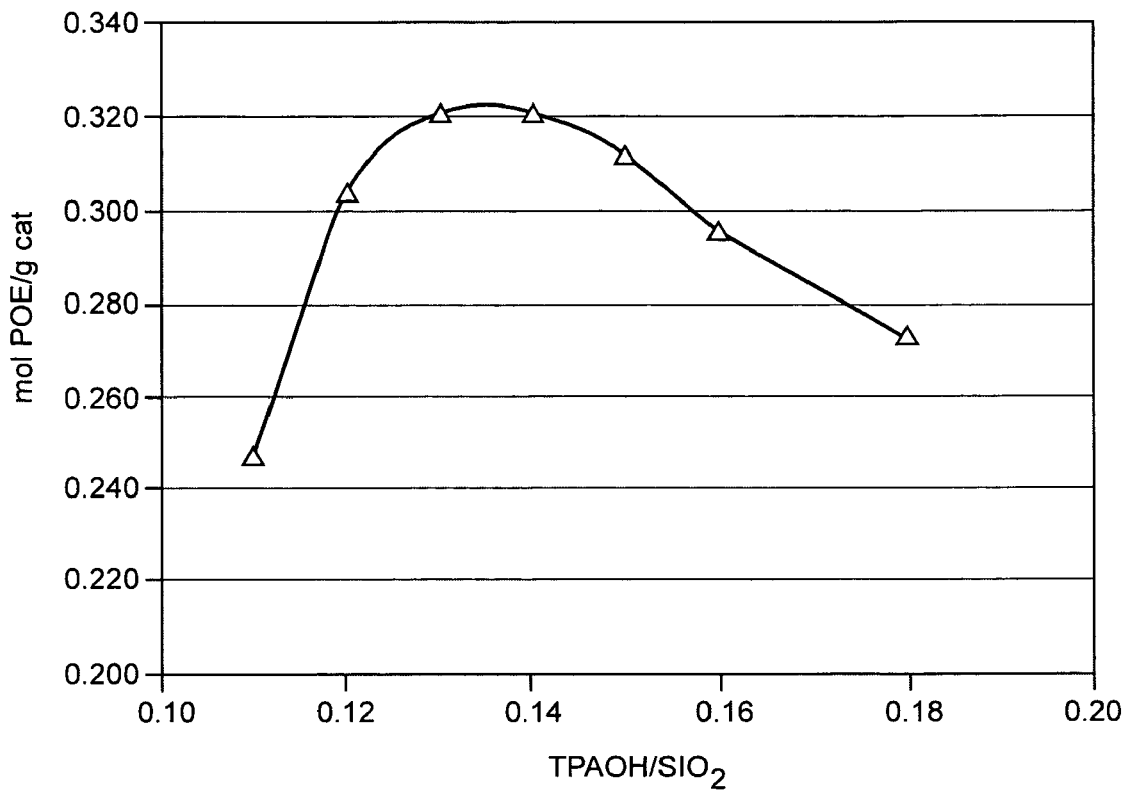
FIG. 1 is a graphical representation of catalytic activity versus the template to $SiO_2$ ratio for catalysts prepared by the invention.

The TS-1 crystals of the present invention are formed in accordance with the generally known technologies described in prior art patents such as U.S. Pat. No. 4,410,501, 6,841,144 or 6,008,389 except that the mol ratio of quaternary ammonium component to $SiO_2$ is not greater than about 0.25 and the rate at which the reaction mixture is ramped (heated) to reaction temperature does not exceed 0.3° C./min. It has further been found that unexpected and especially good results in the production of propylene oxide are achieved with TS-1 catalysts of this invention which are prepared using a mol ratio of quaternary ammonium template to $SiO_2$ in the narrow range of about 0.10 to 0.18 using the said ramp ratios. In the catalyst preparation, a source of titanium such as tetraethyl orthotitanate is provided along with a source of silicon such as tetraethyl orthosilicate. Water and a quaternary ammonium compound such as tetrapropyl ammonium compound are also provided. The components are usually mixed at low temperature, e.g. 0-10° C., heated to room temperature to obtain a homogeneous solution and the resulting solution is slowly heated to the 160-230° C. reaction temperature at a rate not to exceed 0.3° C./min and held at the reaction temperature for a time sufficient for the crystal formation, illustratively 5 hours-2 weeks. Alternatively, the compounds need not be chilled upon mixing but may be maintained at room temperature or higher at the start of ramping.

As used herein, ramp rate refers to the rate at which the feed to the crystallization is heated from an initial temperature which is generally in the range of about 0° C. to 50° C. to the crystallization temperature of 160-230° C. In accordance with the invention, the ramp rate should not exceed 0.3° C./min.

Silicon sources other than tetraethyl orthosilicate can be used. Generally, silica alkoxy compounds, for example compounds where the alkyl group is $C_1$-$C_8$ alkyl group, or mixtures are suitable. Alkoxy silicates which have oligomerized or polymerized can be used such as Silbond-40, ES-40 and the like. Also silica in the form of a high surface area source such as fumed or carbosil, or aerosil products can be used. The titanium compound is suitably a titanium alkoxy compound illustratively where the alkyl group is $C_1$-$C_8$. Also Ti(IV) coordination complexes can be used where the ligands include but are not limited to halogens, acetylacetonates, or carboxylates. Tetrapropyl ammonium hydroxide is the preferred quaternary ammonium template but other materials employing alternate counterions such as halogens, tetrafluoroborates or sulfates could be used. Water in amount which provides a $H_2O/SiO_2$ ratio of about 10 to 200 is used.

The components are admixed and then heated to the 160-230° C., crystal forming reaction temperature at a rate not to exceed 0.3° C./min and held at the reaction temperature for a sufficient time for formation of the product crystals. The crystals are recovered, usually washed, and then calcined to produce the product TS-1.

The TS-1 product formed as indicated above is highly active as a catalyst for the production of propylene oxide wherein propylene is reacted with hydrogen peroxide. Alternatively, a noble metal such as palladium can be deposited by known procedures on the TS-1 to produce a catalyst which is highly active and selective for production of propylene oxide by reaction of propylene, oxygen and hydrogen.

The following examples will serve to illustrate the invention.

EXAMPLE 1

Tetraethyl orthotitanate (20% wt. % Ti) in amount of 2.6 g (0.011 mol) is provided as the source of titanium, tetraethyl orthosilicate in amount of 118.25 g (0.5676 mol) is provided as the source of silicon and tetrapropylammonium hydroxide (40 wt % aqueous solution) in amount of 32.50 g (0.06392 mol) is provided as the template. The mol ratio of template to $SiO_2$ is 0.113.

The above template is diluted with 175.50 g (9.742 mol) g water, chilled to about 5° C., and added to a stirring solution of the titanium and silica source at 4-10° C. The resulting solution is stirred and warmed to room temperature until a homogeneous, transparent solution is obtained. The resulting solution, after being transferred to an autoclave, is heated at a rate sufficient to ramp the solution temperature to 180° C. over a 16 h period (ramp rate of 0.17° C./min). The heated solution is maintained at 180° C. for 10 hours with stirring.

The mixture is cooled to room temperature and centrifuged to recover crystals. The recovered crystals are washed with distilled water (1 time), dried, and calcined in air at 550° C. for 4 hours. The overall yield of zeolite exceeds 95%.

The resulting TS-1 product was tested as a catalyst in the reaction of propylene with hydrogen peroxide to form propylene oxide and was found to form 0.33 mol POE/g catalyst under the test conditions. POE is defined as propylene oxide equivalents and sums all propylene oxide (PO) and products derived from propylene oxide. Selectivities under the conditions described produced PO/POE ratios exceeding 98%. In conducting this test and comparable test in subsequent examples the following procedure was used.

The TS-1 in amount of 0.040 g was slurried in 40 g of a solvent comprised of 5% hydrogen peroxide, 5% water, and 90% methanol. The reaction mixture was allowed to contact in a batch reactor 20 g of propylene for 30 min at a temperature of 50° C. The resultant gas and liquid products were analyzed by chromatography to produce the indicated results.

EXAMPLE 2

Tetraethyl orthotitanate (20% wt % Ti) in amount of 4.125 g (0.01723 mol) is provided as the source of titanium, tetraethyl orthosilicate in amount of 136.2 g (0.6538 mol) is provided as the source of silicon and tetrapropylammonium hydroxide (40 wt % aqueous solution) in amount of 38.78 g (0.07627 mol) is provided as the template. Mol ratio of template to $SiO_2$ is 0.117.

The above template was diluted with 184.58 g (10.25 mol) water, chilled to about 5° C., and added with stirring to a solution of the titanium and silica source at 4-10° C. The resulting solution was stirred and allowed to warm to room temperature until a homogeneous, transparent solution was obtained. The resulting solution, after being transferred to an autoclave, was heated at a rate sufficient to ramp the solution temperature to 180° C. over a 16 h period (0.16° C./min.). The heated solution was maintained at 180° C. for 10 hours with stirring.

The mixture was cooled to room temperature and centrifuged to recover crystals. The recovered crystals were washed with distilled water (1 time), dried, and calcined in air at 550° C. for 4 hours. The overall yield of zeolite exceeds 95%.

The resulting TS-1 product was tested as described in Example 1 as a catalyst in the reaction of propylene with hydrogen peroxide to form propylene oxide and was found to form 0.46 mol POE/g catalyst under the test conditions. Selectivities under the conditions described produced PO/POE ratios exceeding 98%.

EXAMPLE 3

A sample was prepared in all regards as in Example 2 excepting that the ramp time was 12 h to 180° C. (0.20° C./min.). The activity of this material as tested by the procedure described above was 0.41 mol POE/g cat.

EXAMPLE 4

Tetraethyl orthotitanate (20% wt % Ti) in amount of 15.3 g (0.0639 mol) is provided as the source of titanium, tetraethyl orthosilicate in amount of 520.3 g (2.497 mol) is provided as the source of silicon and tetrapropylammonium hydroxide (40 wt % aqueous solution) in amount of 143.0 g (0.2813 mol) is provided as the template provided a mol ratio of template to $SiO_2$ of about 0.113.

The above template was diluted with 772.2 g (42.86 mol) water, chilled to about 5° C., and added with stirring to solution of the titanium and silica source at 4-10° C. The resulting solution was stirred and allowed to warm to room temperature until a homogeneous, transparent solution was obtained. Samples of the resulting solution, after being transferred to an autoclave, were heated at a rate sufficient to ramp the solution temperature to 190° C. over a range of times of from 12 to 20 h (0.23-0.14° C./min). The heated solution was maintained at 190° C. for 10 hours with stirring.

The mixture was cooled to room temperature and centrifuged to recover crystals. The recovered crystals were washed with distilled water (1 time), dried, and calcined in air at 550° C. for 4 hours. The overall yield of zeolite exceeds 95%.

The resulting TS-1 product was tested as a catalyst in the reaction of propylene with hydrogen peroxide to form propylene oxide as described in Example 1 and was found to form >0.39 mol POE/g catalyst under the test conditions. Selectivities under the conditions described produced PO/POE ratios exceeding 98%.

COMPARATIVE EXAMPLE 1

A sample from the batch of gel solution from Example 3 was crystallized as above excepting that the ramp time was 8 h to 190° C. (0.354° C./min). The activity of this material as tested as described in Example 1 was 0.36 mol POE/g cat. The superiority of the Example 3 catalyst demonstrates the advantages achieved through the invention.

EXAMPLE 5

Tetraethyl orthotitanate (20% wt Ti) in amount of 3.54 g (0.0148 mol) is provided as the source of titanium, tetraethyl orthosilicate in amount of 118.3 g (0.568 mol) is provided as the source of silicon and tetrapropylammonium hydroxide (40 wt % aqueous solution) in amount of 32.50 g (0.06392 mol) is provided as the template. The mol ratio of template to $SiO_2$ is 0.11.

The above template was diluted with 175.5 g (9.74 mol) water, chilled to about 5° C., and added to a stirring solution of the tianium and silica source at 4-10° C. The resulting solution was allowed to stir and warm to room temperature until a homogeneous, transparent solution was obtained. The resulting solution, after being transferred to an autoclave, was heated at a rate sufficient to ramp the solution temperature to 180° C. over a 16 h period (0.16° C./min.). The heated solution was maintained at 180° C. for 10 hours with stirring.

The mixture was cooled to room temperature and centrifuged to recover crystals. The recovered crystals were washed with distilled water (1 time), dried, and calcined in air at 550° C. for 4 hours. The overall yield of zeolite exceeds 95%.

The resulting TS-1 product was tested as a catalyst in the reaction of propylene with hydrogen peroxide to form propylene oxide and was found to form 0.41 mol POE/g catalyst under the test conditions. Selectivities under the conditions described produced PO/POE ratios exceeding 98%. In conducting these tests the following procedure was used.

When compared to the results achieved according to Example 2 (mol ratio template to $SiO_2$ of 0.12) these results illustrate that only very small ratio changes markedly affect the catalytic properties of the TS-1.

EXAMPLE 6

The TS-1 preparation procedures were scaled up to a 15 gallon scale and in a series of runs at different template to $SiO_2$ ratios the catalyst activity was determined as above. In each case the ramp rate was 0.14° C./min. The results obtained are depicted in FIG. 1 and clearly demonstrate surprising and the superior results which are achieved with mol ratios of template to $SiO_2$ in the range 0.12 to 0.18.

A pair of experiments were carried out at differing template to silicon compound ratios and differing ramp rates with TS-1 products having essentially the same crystal size.

Specifically, catalyst A was prepared in accordance with the invention at a template to $SiO_2$ mol ratio of 0.14 and a ramp rate to 180° C. of 0.15° C./min. Catalyst B, on the other hand, had a template to $SiO_2$ mol ratio of 0.45 and a ramp rate to 180° C. of 0.49° C./min. Although in each case the same solution concentration of the titanium component was used the catalyst B analyzed slightly lower in Ti content.

The catalyst A and B TS-1 crystals had essentially the same average particle size, 0.2 to 0.3 microns.

When tested as described above the results presented in the following Table were obtained:

| Table | | |
|---|---|---|
| Activity | Catalyst A | Catalyst B |
| $H_2O_2$ conversion (%) | 35 | 26 |
| MolPOE/g cat | 0.46 | 0.34 |
| MolPO/g cat | 0.45 | 0.34 |
| PO/POE (%) | 98 | 98 |

From these results it can be seen that the TS-1 (catalyst A) prepared according to the invention was greatly superior in activity to produce PO and POE that was TS-1 of the same particle size not prepared by the invention (catalyst B).

Frequently it is useful to deposit a noble metal on the TS-1 prepared by the invention in order to form a catalyst useful for the reaction of propylene, oxygen and hydrogen to form propylene oxide. Procedures useful in the preparation of the noble metal TS-1 catalysts are well known in the art and are described, for example, in U.S. Pat. No. 6,555,493.

EXAMPLE 7

Using TS-1 prepared as described in Example 1 a catalyst comprised of 0.45 wt % Pd on TS-1 was prepared by the procedure described in Example 1 of U.S. Pat. No. 6,555,493.

The catalyst was used for production of propylene oxide by reaction of propylene, oxygen and hydrogen as described in Example 1 of U.S. Pat. No. 6,555,493.

The catalyst evidenced superior activity and selectivity in the product of PO and POE.

EXAMPLE 8

A catalyst was prepared as generally described in Example 1, having a template to $SiO_2$ ratio of 0.13 and containing 2.5 wt % Ti. Samples were ramped to 180° C. at varying rates and held for 10 hours. Both TS-1 crystal size and catalytic activity were measured and the results are depicted graphically in FIG. 2.

Figure 2:
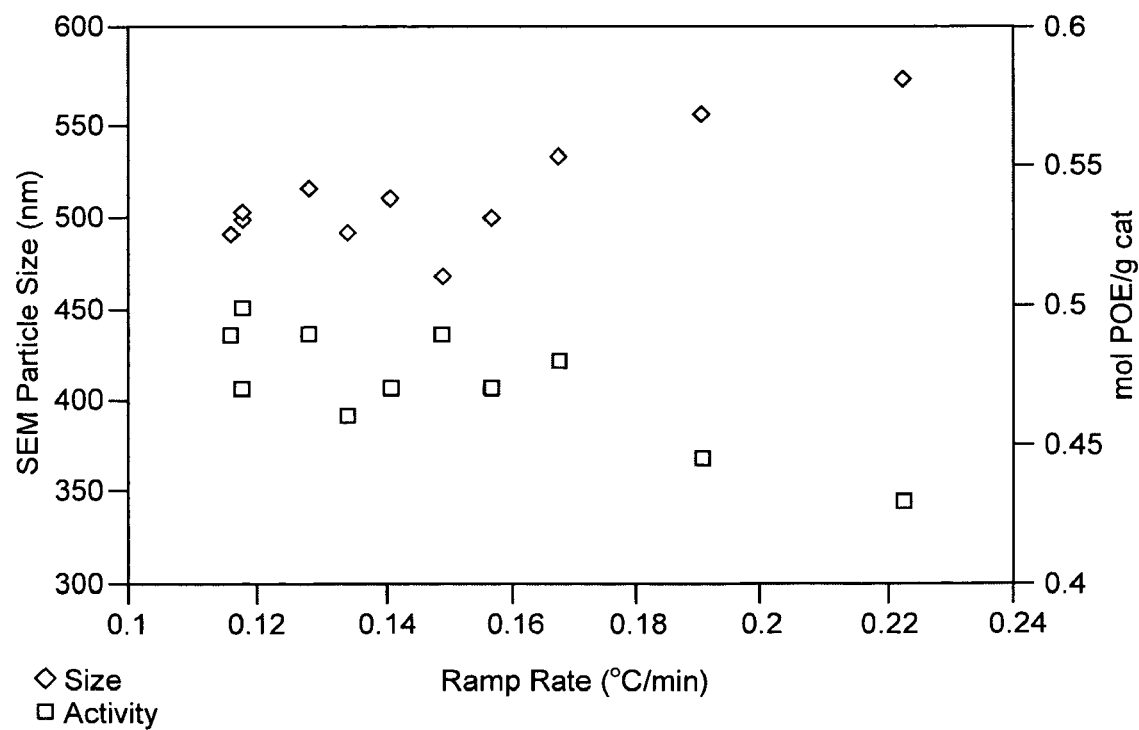
FIG. 2 is a graphical representation of the effect of ramp rate on both TS-1 crystal particle size and catalytic activity.

It can be seen from FIG. 2 that the catalyst activity generally declined as ramp rate increased and that TS-1 crystal size generally increased as the ramp rate increased.

The effect of ramp rate on both catalytic activity and crystal size is believed to be novel and unexpected.

We claim:

1. A process for the preparation of titanium silicalite crystals useful as catalyst for the production of propylene oxide which comprises forming an aqueous solution of a silica source, a titanium source and a template, heating the said solution to a temperature in the range of 160-230° C. at the rate not to exceed 0.3° C./min, and maintaining the heated mixture at 160-230° C. for a time sufficient for the formation of titanium silicalite crystals.

2. A process for the preparation of titanium silicalite crystals useful as catalyst for the production of propylene oxide which comprises forming an aqueous solution of a silica source selected from the group consisting of tetra alkyl orthosilicates, alkoxy silicates, and silica, a titanium source selected from the group consisting of tetra alkyl orthotitanates, titanium alkoxy compounds, and Ti(IV) coordination complexes where the ligands include halogens, acetylacetonates or carboxylates and a quaternary ammonium compound template, the mol ratio of template to silica source not exceeding 0.25, heating the said solution to a temperature in the range of 160-230° C. at a rate not to exceed 0.3° C./min, and maintaining the heated mixture at 160-230° C. for a time sufficient for the formation of titanium silicalite crystals.

3. The process of claim 2 wherein the mol ratio of template to silica source is 0.10-0.18.

4. The process of claim 2 wherein tetraypropylammonium hydroxide is the template.

5. The process of claim 2 wherein the silica source is tetra alkyl orthosilicate.

6. The process of claim 2 wherein the titanium source is tetra alkyl orthotitanate.

7. The process for the production of propylene oxide which comprises oxidizing propylene using the catalyst prepared by the method of claim 2.

8. A process for the preparation of titanium silicalite crystals useful as catalyst for the production of propylene oxide which comprises forming an aqueous solution of a tetra alkyl orthosilicate, a tetra alkyl orthotitanate, and a quaternary ammonium compound template, the mole ratio of template to tetra alky orthosilicate not exceeding 0.25, heating the said solution to a temperature in the range of 160-230° C. at a rate not to exceed 0.3° C./min, and maintaining the heated solution at 160-230° C. for a time sufficient for the formation of titanium crystals.

* * * * *